(12) United States Patent
Cameron et al.

(10) Patent No.: US 8,455,049 B2
(45) Date of Patent: Jun. 4, 2013

(54) STRONTIUM PRECURSOR FOR USE IN CHEMICAL VAPOR DEPOSITION, ATOMIC LAYER DEPOSITION AND RAPID VAPOR DEPOSITION

(75) Inventors: Thomas M. Cameron, Newtown, CT (US); Chongying Xu, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 220 days.

(21) Appl. No.: 12/672,684

(22) PCT Filed: Aug. 3, 2008

(86) PCT No.: PCT/US2008/072045
§ 371 (c)(1),
(2), (4) Date: Jul. 26, 2010

(87) PCT Pub. No.: WO2009/020888
PCT Pub. Date: Feb. 12, 2009

(65) Prior Publication Data
US 2010/0291299 A1    Nov. 18, 2010

Related U.S. Application Data

(60) Provisional application No. 60/954,581, filed on Aug. 8, 2007.

(51) Int. Cl.
*C23C 16/44* (2006.01)
*C07F 3/00* (2006.01)

(52) U.S. Cl.
USPC .................................. 427/248.1; 260/665 R

(58) Field of Classification Search
None
See application file for complete search history.

(56) References Cited

U.S. PATENT DOCUMENTS

| | | |
|---|---|---|
| 4,915,988 A | 4/1990 | Erbil |
| 4,927,670 A | 5/1990 | Erbil |
| 4,948,623 A | 8/1990 | Beach et al. |
| 4,960,916 A | 10/1990 | Pazik |
| 4,962,214 A | 10/1990 | Villacorta et al. |
| 5,204,314 A | 4/1993 | Kirlin et al. |
| 5,225,561 A | 7/1993 | Kirlin et al. |
| 5,280,012 A | 1/1994 | Kirlin et al. |
| 5,453,494 A | 9/1995 | Kirlin et al. |
| 5,536,323 A | 7/1996 | Kirlin et al. |
| 5,555,154 A | 9/1996 | Uchikawa et al. |
| 5,711,816 A | 1/1998 | Kirlin et al. |

(Continued)

FOREIGN PATENT DOCUMENTS

| | | | |
|---|---|---|---|
| EP | 1645656 | * | 4/2006 |
| EP | 1798307 A1 | | 12/2006 |

(Continued)

OTHER PUBLICATIONS

Kosolo, App Surf Sci, V211, 2003, p. 102.*

(Continued)

*Primary Examiner* — Joseph Miller, Jr.
(74) *Attorney, Agent, or Firm* — Hultquist, PLLC; Steven J. Hultquist; Maggie Chappuis

(57) ABSTRACT

A method of depositing a crystalline strontium titanate film on a substrate is provided, comprising carrying out an atomic layer deposition (ALD) process with strontium and titanium precursors, wherein the strontium precursor is bis(n-propyltetramethylcyclopentadienyl)strontium.

5 Claims, 2 Drawing Sheets

U.S. PATENT DOCUMENTS

| | | | |
|---|---|---|---|
| 5,840,897 | A | 11/1998 | Kirlin et al. |
| 5,919,522 | A | 7/1999 | Baum et al. |
| 6,110,529 | A | 8/2000 | Gardiner et al. |
| 6,111,122 | A | 8/2000 | Paw et al. |
| 6,177,558 | B1 | 1/2001 | Brennan et al. |
| 6,218,518 | B1 | 4/2001 | Baum et al. |
| 6,277,436 | B1 | 8/2001 | Stauf et al. |
| 6,340,386 | B1 | 1/2002 | Hendrix et al. |
| 6,506,666 | B2 | 1/2003 | Marsh |
| 6,511,706 | B1 | 1/2003 | Hendrix et al. |
| 6,599,447 | B2 | 7/2003 | Stauf et al. |
| 6,646,122 | B1 | 11/2003 | Nuhlen et al. |
| 6,660,331 | B2 | 12/2003 | Hendrix et al. |
| 6,787,186 | B1 | 9/2004 | Hintermaier |
| 6,984,591 | B1 | 1/2006 | Buchanan et al. |
| 6,989,457 | B2 | 1/2006 | Kamepalli et al. |
| 7,108,747 | B1 | 9/2006 | Leskela et al. |
| 7,250,367 | B2 | 7/2007 | Vaartstra et al. |
| 7,635,441 | B2 | 12/2009 | Kadokura et al. |
| 2002/0004266 | A1 | 1/2002 | Hashimoto et al. |
| 2002/0090815 | A1 | 7/2002 | Koike et al. |
| 2003/0012876 | A1 | 1/2003 | Min et al. |
| 2003/0072882 | A1 | 4/2003 | Niinisto et al. |
| 2004/0038808 | A1 | 2/2004 | Hampden-Smith et al. |
| 2004/0197946 | A1 | 10/2004 | Vaartstra et al. |
| 2004/0211998 | A1 | 10/2004 | Araujo et al. |
| 2005/0009325 | A1 | 1/2005 | Chung et al. |
| 2005/0208699 | A1 | 9/2005 | Furkay et al. |
| 2005/0217575 | A1 | 10/2005 | Gealy et al. |
| 2006/0006449 | A1 | 1/2006 | Jeong et al. |
| 2006/0027451 | A1 | 2/2006 | Park et al. |
| 2006/0035462 | A1 | 2/2006 | Millward |
| 2006/0049447 | A1 | 3/2006 | Lee et al. |
| 2006/0115595 | A1 | 6/2006 | Shenai-Khatkhate et al. |
| 2006/0138393 | A1 | 6/2006 | Seo et al. |
| 2006/0172067 | A1 | 8/2006 | Ovshinsky et al. |
| 2006/0172083 | A1 | 8/2006 | Lee et al. |
| 2006/0180811 | A1 | 8/2006 | Lee et al. |
| 2007/0154637 | A1 | 7/2007 | Shenai-Khatkhate et al. |
| 2008/0254218 | A1 | 10/2008 | Lei et al. |
| 2009/0074965 | A1 | 3/2009 | Xu et al. |
| 2009/0087561 | A1 | 4/2009 | Chen et al. |
| 2009/0215225 | A1 | 8/2009 | Stender et al. |
| 2009/0275164 | A1 | 11/2009 | Chen et al. |
| 2009/0321733 | A1 | 12/2009 | Gatineau et al. |
| 2010/0062150 | A1 | 3/2010 | Xu et al. |

FOREIGN PATENT DOCUMENTS

| | | |
|---|---|---|
| EP | 2 000 561 A1 | 12/2008 |
| JP | 10-273779 A1 | 10/1998 |
| JP | 2006-037123 A | 2/2006 |
| SU | 768457 A | 10/1980 |
| WO | 0015865 A1 | 3/2000 |
| WO | 0166834 A2 | 9/2001 |
| WO | 2004046417 A2 | 6/2004 |
| WO | 2006012052 A2 | 2/2006 |

OTHER PUBLICATIONS

Anderson, Q. et al., "Synthesis and Characterization of the First Pentaphenylcyclopentadienyl Copper Complex (Ph5CP)Cu(PPh3)", "Organometallics", 1998, pp. 4917-4920, vol. 17.

Artaud-Gillet, M.C. et al., "Evaluation of copper organometallic sources for CuGaSe2 photovoltaic applications", "Journal of Crystal Growth", 2003, pp. 163-168, vol. 248.

Ren, H. et al., "Sythesis and structures of cyclopentadienyl N-heterocyclic carbene copper complexes", "Journal of Organometallic Chemistry", 2006, pp. 4109-4113, vol. 691.

Hatanpaa, Timo, et al., "Synthesis and characterisation of cyclopentadienyl complexes of barium: precursors for atomic layer deposition of BaTiO3", "Dalton Trans.", 2004, pp. 1181-1188, No. 8.

Holme, T. et al., "Atomic Layer Deposition and Chemical Vapor Deposition Precursor Selection Method Application to Strontium and Barium . . . ", "J. Phys. Chem.", Jul. 27, 2007, pp. 8147-8151, vol. 111, No. 33, Publisher: American Chemical Society.

Kirlin, Peter S., et al., "Growth of High Tc YBaCuO Thin Films by Metalorganic Chemical Vapor Deposition", "SPIE", 1988, pp. 115-127, vol. 1187.

Kirlin, Peter S., et al., "Thin Films of Barium Fluoride Scintillator Deposited by Chemical Vapor Deposition", "Nuclear Instruments and Methods in Physics Research", 1990, pp. 261-294, vol. A, No. 289.

Leskela, Markku, et al., "Atomic layer deposition chemistry: recent developments and future challenges", "Angew. Chem. Int. Ed.", 2003, pp. 5548-5554, vol. 42.

Macomber, D. et al., "n5- Cyclopentadienyl- and n5-Pentamethylcyclopentadienyl copper compunds Continng Phosphine, Carbonyl, and n2-Acetyle", "J. Am. Chem.", 1983, pp. 5325-5329, vol. 105.

McCormick, M. et al., "Solution Synthesis of Calcium, Strontium, and Barium Metallocenes", "Polyhedron", 1988, pp. 725-730, vol. 7, No. 9.

Papadatos, Filippos, et al., "Characterization of Ruthenium and Ruthenium Oxide Thin Films deposited by Chemical Vapor Deposition for CMOS Gate . . . ", "Mat. Res. Soc. Symp. Proc.", 2003, pp. N3.3.1-N3.3.6, vol. 745.

Vehkamaki, Marko, et al., "Atomic Layer Deposition of SrTiO3 Thin Films from a Novel Strontium Precursor-Strontium-bis(tri-isopropyl cyclopentadien", "Chem. Vapor Dep.", Mar. 2001, pp. 75-80, vol. 7, No. 2.

Selg, P. et al., "Solution Infrared Spectroscopic Studies on Equilibrium Reactions of CO With the Decamethylmetallocenes CP2MII, Where . . .", "Organometallics", Jun. 22, 2002, pp. 3100-3107, vol. 21.

Singh, R. et al., "In-Situ Processing of Epitaxial Y-Ba-Cu-O High Tc Superconducting Films on (100) SrTiO3 and 100 YS-ZrO2 Substrates", "Applied Physics Letters", May 1989, pp. 2271-2273, vol. 54, No. 22.

Vehkamaki, Marko, et al., "Growth of SrTiO3 and BaTiO3 Thin Films by Atomic Layer Deposition", "Electrochem. Solid-State Lett.", Oct. 1999, pp. 504-506, vol. 2, No. 10.

Unpublished U.S. Appl. No. 12/990,459.

Unpublished U.S. Appl. No. 11/949,874.

Christen, H., et al., "Semiconducting epitaxial films of metastable SrRu0.5Sn0.5O3 grown by pulsed laser deposition", "Applied Physics Letters", 1997, pp. 2147-2149 (Title and Abstract), vol. 70, No. 16.

Kvyatkovskii, O., "On the Nature of Ferroelectricity in Sr1-xAxTiO3 and KTa1-xNbxO3 Solid Solutions", "Physics of the Solid State", 2002, pp. 1135-1144, vol. 44, No. 6.

Lu, H., et al., "Evolution of itinerant ferromagnetism in SrxPb1-xRuO3 ($0 \leqq x \leqq 1$): Interplay between Jahn-Teller distortion and A-site disorder", "Applied Physics Letters", Mar. 22, 2011, pp. 1-3, vol. 98, No. 122503.

Niinistoe, J., et al., "Atomic Layer Deposition of High-k Oxides of the Group 4 Metals for Memory Applications", "Advanced Engineering Materials", Mar. 9, 2009, pp. 223-234, vol. 11, No. 4.

Wu, L., et al., "Humidity Sensitivity of Sr(Sn, Ti)03 Ceramics", "Journal of Electronic Materials", 1990, pp. 197-200, vol. 19, No. 2.

* cited by examiner

STRONTIUM PRECURSOR FOR USE IN CHEMICAL VAPOR DEPOSITION, ATOMIC LAYER DEPOSITION AND RAPID VAPOR DEPOSITION

CROSS-REFERENCE TO RELATED APPLICATIONS

The present application is a U.S. national phase under the provisions of 35 U.S.C. §371 of International Application No. PCT/US08/72045 filed Aug. 3, 2008, which in turn claims the benefit of priority under 35 USC 119 of U.S. Provisional Patent Application No. 60/954,581 filed Aug. 8, 2007. The disclosures of said international application and said U.S. provisional patent application are hereby incorporated herein by reference, in their respective entireties, for all purposes.

FIELD OF THE INVENTION

The present invention relates to precursors for use in depositing strontium- and barium-containing films on substrates such as wafers or other microelectronic device substrates, as well as associated processes of making and using such precursors, and source packages of such precursors.

DESCRIPTION OF THE RELATED ART

In the manufacture of microelectronic devices, conformal, high k materials based on barium (Ba) or strontium (Sr), such as strontium titanate (STO) and barium strontium titanate (BST), are deposited on substrates by deposition techniques such as chemical vapor deposition (CVD), atomic layer deposition (ALD) and rapid vapor deposition (RVD).

Such deposition requires monomeric metal precursors that are transportable (volatile) at temperatures specific to the deposition process.

In addition to this requirement, it is advantageous in many applications for the precursors to be in liquid form at the delivery temperature used in the deposition process. For example, the precursors should have melting points below the operating temperature of the vaporizer that is used in a liquid delivery deposition process system, to avoid clogging of the vaporizer and to minimize the potential for particle generation by the vaporizer. Such clogging and particle generation issues are particularly common when solutions of solid precursors are used in deposition.

Another problem associated with many conventional barium and strontium precursors is their sensitivity to oxygen and moisture, which cause degradation of these precursors, and increase the handling difficulties of such precursors.

It would therefore be a substantial advance in the art to provide barium and strontium precursors having low melting point, e.g., below 130° C., to minimize and preferably avoid the aforementioned clogging and particle generation problems, that have good transport and deposition properties for forming conformal films on substrates, and that have good handling characteristics and stability with respect to oxygen and moisture.

SUMMARY OF THE INVENTION

The present invention relates to barium and strontium precursors useful in chemical vapor deposition, atomic layer deposition and rapid vapor deposition applications, to form corresponding metal-containing films on substrates, as well as associated processes and packaged forms of such precursors.

In one aspect, the invention relates to a metal precursor selected from among:

(i) precursors of the formula Cp-M-Cp
wherein:
M is a metal center selected from among Ba or Sr;
Cp is cyclopentadienyl having substituents $R^1$, $R^2$, $R^3$, $R^4$ and $R^5$ on respective ring carbon atoms thereof; and
each $R^1$, $R^2$, $R^3$, $R^4$, and $R^5$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^a R^b R^c NNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center;

(ii) precursors of the formula Ind-M-Ind
wherein:
M is a metal center selected from among Ba or Sr;
Ind is indenyl having substituents $R^1$, $R^2$, $R^3$, $R^4$, $R^6$, $R^7$, $R^8$ and $R^9$ on respective ring carbon atoms thereof; and
each $R^1$, $R^2$, $R^3$, $R^4$, $R^6$, $R^7$, $R^8$ and $R^9$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^a R^b R^c NNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center;

(iii) precursors of the formulae MCpX, M(Ind)X and M(Cp)(Ind)
wherein:
M is a metal center selected from among Ba or Sr;
Cp is cyclopentadienyl having substituents $R^1$, $R^2$, $R^3$, $R^4$, and $R^5$ on respective ring carbon atoms thereof;
Ind is indenyl having substituents $R^1$, $R^2$, $R^3$, $R^4$, $R^6$, $R^7$, $R^8$ and $R^9$ on respective ring carbon atoms thereof;
each $R^1$, $R^2$, $R^3$, $R^4$, $R^6$, $R^7$, $R^8$ and $R^9$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^a R^b R^c NNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center; and
X is a coordinating ligand selected from among $C_1$-$C_{12}$ alkyl, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, perfluoroalkyl, and silicon-containing groups selected from the group consisting of silyl, alkylsilyl, perfluoroalkylsilyl, triarylsilyl and alkylsilylsilyl, beta-diketonate or a corresponding sulfur or nitrogen compound, halide, amide, alkoxide, carboxylate, Schiff base and pendant ligands including functional group(s) providing further coordination to the metal center; and (iv) Lewis-base and neutral ligand adducts of precursors (i), (ii) and (iii).

In another aspect, the invention relates to bis(n-propyltetramethyl-cyclopentadienyl)barium and Lewis base adducts thereof.

A further aspect of the invention relates to bis(n-propyltetramethyl-cyclopentadienyl)strontium and Lewis base adducts thereof.

Yet another aspect of the invention relates to a Lewis base-stabilized strontium cyclopentadienyl complex of the formula:

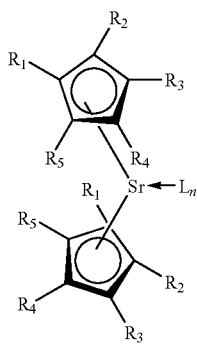

in which:

L is a Lewis base ligand;

n is the number of Lewis base ligands coordinated to the Sr central atom, and is an integer having a value of from 1 to 4; and each $R_1$, $R_2$, $R_3$, $R_4$ and $R_5$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^aR^bR^cNNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to Sr.

In a further aspect, the invention relates to a method of forming a metal-containing film on a substrate, wherein said metal comprises a metal species selected from among barium and strontium, said method comprising volatilizing a metal precursor according to claim 1, to form a precursor vapor, and contacting said precursor vapor with a substrate to form of said metal-containing film thereon.

A further aspect of the invention relates to a precursor composition comprising at least one metal precursor of the invention, and a solvent medium for the metal precursor(s).

A still further aspect of the invention relates to a precursor vapor of a metal precursor of the invention.

Another aspect of the invention relates to a precursor source package comprising a precursor storage and dispensing vessel containing a metal precursor of the invention.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
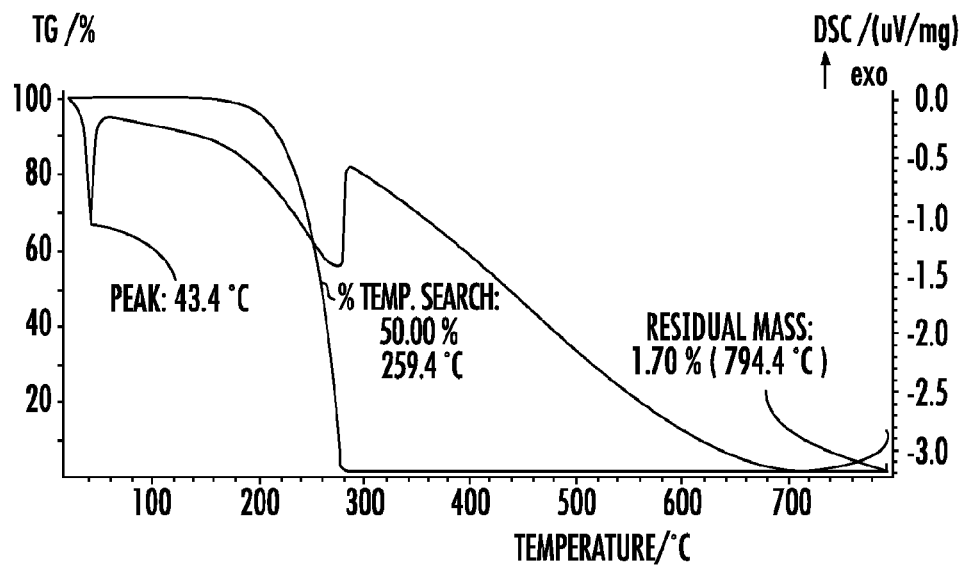
FIG. 1 is a simultaneous thermal analysis (STA) plot of thermogravimetric analysis (TGA) and differential scanning calorimetry (DSC) curves for bis(n-propyltetramethyl-cyclopentadienyl)strontium.

The present invention relates in various aspects to barium and strontium metal precursors having low melting point, characterized by superior stability, and utility for forming highly conformal films. The superior air stability of such precursors also minimizes generation of particles in the CVD/ALD/RVD processes in which such precursors are usefully employed to form barium- and/or strontium-containing films.

Although the ensuing discussion is directed primarily to barium and/or strontium precursors, the invention also contemplates the provision of corresponding precursors with other Group II metal species, such as calcium.

Metal precursors of the invention include those selected from among:

(i) precursors of the formula Cp-M-Cp wherein:

M is a metal center selected from among Ba or Sr;

Cp is cyclopentadienyl having substituents $R^1$, $R^2$, $R^3$, $R^4$ and $R^5$ on respective ring carbon atoms thereof; and each $R^1$, $R^2$, $R^3$, $R^4$ and $R^5$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl (such term being intended to be broadly construed to include substituents containing linear, branched, and/or cyclic moieties containing ethylenic unsaturation, e.g., vinyl, allyl, cyclic-ene species, etc., and substituents containing various types of such moieties therein, e.g., tetramethyl-pentadienylvinyl), $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^aR^bR^cNNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center;

(ii) precursors of the formula Ind-M-Ind wherein:

M is a metal center selected from among Ba or Sr;

Ind is indenyl having substituents $R^1$, $R^2$, $R^3$, $R^4$, $R^6$, $R^7$, $R^8$ and $R^9$ on respective ring carbon atoms thereof; and each $R^1$, $R^2$, $R^3$, $R^4$, $R^6$, $R^7$, $R^8$ and $R^9$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^aR^bR^cNNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center;
(iii) precursors of the formulae MCpX, M(Ind)X and M(Cp)(Ind) wherein:
M is a metal center selected from among Ba or Sr;
Cp is cyclopentadienyl having substituents $R^1$, $R^2$, $R^3$, $R^4$, and $R^5$ on respective ring carbon atoms thereof;
Ind is indenyl having substituents $R^1$, $R^2$, $R^3$, $R^4$, $R^6$, $R^7$, $R^8$ and $R^9$ on respective ring carbon atoms thereof;
each $R^1$, $R^2$, $R^3$, $R^4$, $R^6$, $R^7$, $R^8$ and $R^9$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^aR^bR^cNNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center; and
X is a coordinating ligand selected from among $C_1$-$C_{12}$ alkyl, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, perfluoroalkyl, and silicon-containing groups selected from the group consisting of silyl, alkylsilyl, perfluoroalkylsilyl, triarylsilyl and alkylsilylsilyl, beta-diketonate or a corresponding sulfur or nitrogen compound, halide, amide, alkoxide, carboxylate, Schiff base and pendant ligands including functional group(s) providing further coordination to the metal center; and
(iv) Lewis-base and neutral ligand adducts of precursors (i), (ii) and (iii).

X may in various embodiments comprise specific ligand species described in U.S. Pat. No. 7,108,747, and the complexing species forming adducts may comprise specific ligands described in U.S. Pat. No. 7,108,747. Neutral ligand adducts, e.g., of the formula $L_n$, include ligands that bind to the central metal by either one or several of its atoms, where n depicts the number of the ligands being bound. Neutral adduct ligands include ligands as described in such U.S. Pat. No. 7,108,747.

The pendant ligands including functional group(s) providing further coordination to the metal center may in various embodiments of the invention include ligands selected from among aminoalkyl, alkoxyalkyl, aryloxyalkyl, imidoalkyl, and acetylalkyl Ligands may in specific embodiments be selected from among:
(A) aminoalkyls of the following formulae:

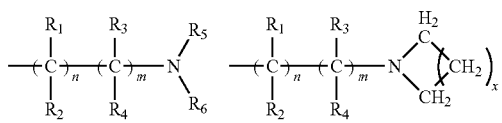

wherein each of $R_1$-$R_4$ is the same as or different from one another, with each being independently selected from among hydrogen and $C_1$-$C_6$ alkyl and $C_6$-$C_{10}$ aryl; each of $R_5$ and $R_6$ is the same as or different from the other, with each being independently selected from among $C_1$-$C_6$ alkyl; n and m are each selected independently from 0 to 4 with the proviso that m and n cannot be 0 at the same time, and x is selected from 1 to 5;

(B) alkoxyalkyls and aryloxyalkyls of the following formulae:

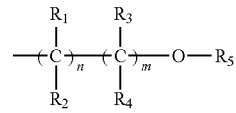

wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

(C) imidoalkyl of the formula:

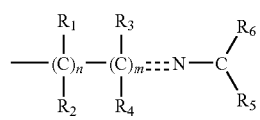

wherein each of $R_1$-$R_6$ is the same as or different from one another, with each being independently selected from among hydrogen, $C_1$-$C_6$ alkyl, and $C_6$-$C_{10}$ aryl; and n and m are selected independently from 0 to 4, with the proviso that m and n cannot be 0 at the same time;

(D) acetylalkyls of the formula:

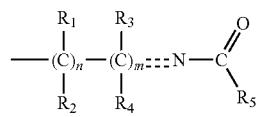

wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

Metal precursors of the invention, in another aspect thereof, include those selected from among strontium and barium bis(n-propyltetramethylcyclopentadienyl) complexes (I) and strontium and barium isopropylated indenyl complexes (II):

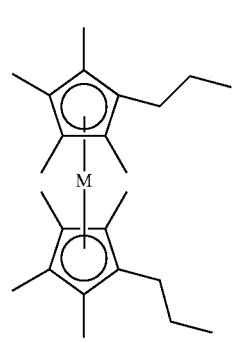

I

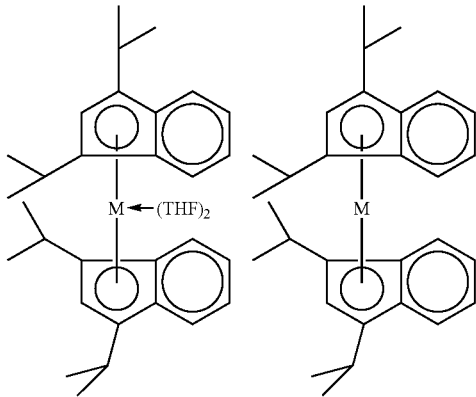

wherein M is Ba or Sr, and THF is tetrahydrofuran.

Such precursors have low melting points (<130° C.), good transport and deposition properties for forming conformal films on substrates, and good handling characteristics and stability with respect to oxygen and moisture.

Bis(n-propyltetramethylcyclopentadienyl)strontium, for example, has a melting point of 43.4° C. The simultaneous thermal analysis (STA) plot of thermogravimetric analysis (TGA) and differential scanning calorimetry (DSC) curves for such precursor is shown in FIG. 1 hereof.

In another aspect, the invention relates to Lewis-base stabilized strontium and barium cyclopentadienyl complexes that are useful for CVD, ALD and RVD applications, which the metal central atom of the precursor compound is coordinated with one or more Lewis base ligands to form corresponding stabilized complexes of Ba or Sr. Preferably, when more than one Lewis base ligand is present, each of the ligands is the same as the other(s).

Such Lewis base ligands stabilize the complex against degradation by oxygen and/or moisture in exposure to air, and thus provide more easily handled precursor compositions, relative to various barium and strontium source reagents of the prior art.

In a specific aspect, the invention relates to Lewis base adducts of the dicyclopentadienyl or diindenyl compounds of the invention, wherein the dicyclopentadienyl or diindenyl compound is an oil at standard temperature and pressure (25° C. and 1 atmosphere) conditions. An illustrative adduct of such type is $Sr(Cp')_2(PMDETA)$, wherein Cp'=tetramethyl-n-propylcyclopentadienyl, and PMDETA is pentamethyl diethylene triamine(N-[2-(dimethylamino)ethyl]N,N',N'-trimethyl-1,2-ethanediamine).

A specific strontium cyclopentadienyl compound of the invention comprises $SrCp_2$ which can for example be formed from $SrCp_2G$ adducts, wherein the adducting species G can for example be tetrahydrofuran or ether, e.g., $SrCp_2(THF)_4$ where THF is tetrahydrofuran.

The Lewis base ligands used to form adducts and complexes of the invention can be of any suitable type, and include, without limitation, multidentate glymes such as dimethoxyethane and tetraglyme, nitrogen-containing multidentate ligands such as PMDETA, and monocoordinate ligands such as pyridine and tetrahydrofuran. The Lewis base ligands enhance compound stability by protecting the metal centers via steric crowding (encapsulation) and by providing electron density to the metal center. Lewis bases such as alkene, diene, cycloalkene, cyclodiene, cyclooctatetraene, alkyne, substituted alkyne (symmetrical or asymmetrical), amine, diamine, triamine, tetraamine, ether, tetrahydrofuran, glyme, diglyme, triglyme, tetraglyme, phosphine, carbonyl, dialkyl sulfide, vinyltrimethylsilane, and allyltrimethylsilane can be used.

Precursor compounds stabilized in such fashion exhibit an enhanced robustness and suitability for deposition processes. Precursors in which the central atom in the complex is Sr are particularly useful in ALD processes for forming strontium titanate (STO) films, when such complex and a titanium precursor are employed as the alternating vapor-phase precursors contacted with the substrate. Strontium precursors of the invention, e.g., $Sr(Cp)_2$, may also be employed to form strontium ruthenium oxide (SrRuOx) films. SrRuOx is a conductive oxide and may be employed as an electrode material for STO or barium strontium titanate (BST) devices. In various embodiments, the films of the invention can be doped with suitable dopant species, e.g., Nb, Zr, As, etc. and other barium- and/or strontium-containing films can be formed using the Ba and Sr precursors of the invention, including strontium tantalate, barium strontium zirconium titanate, ruthenium strontiate, etc.

The precursors of the invention may also be employed to form BST films, when respective barium and strontium precursors are utilized, in combination with a suitable titanium precursor. For this purpose, titanium precursors such as those described in U.S. Pat. No. 7,108,747 can be advantageously employed.

An illustrative Lewis base-stabilized strontium cyclopentadienyl complex of the invention is shown below:

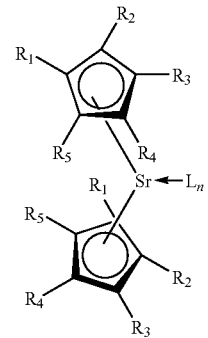

in which:
L is a Lewis base ligand;
n is the number of Lewis base ligands coordinated to the Sr central atom, and is an integer having a value of from 1 to 4; and
each $R_1, R_2, R_3, R_4$ and $R_5$ is the same as or different from one another, with each being independently selected from among H, $C_1$-$C_{12}$ alkyl, $C_1$-$C_{12}$ amino, $C_1$-$C_{12}$ alkylamino, $C_1$-$C_{12}$ alkoxy, $C_3$-$C_{10}$ cycloalkyl, $C_2$-$C_{12}$ alkenyl, $C_7$-$C_{12}$ aralkyl, $C_7$-$C_{12}$ alkylaryl, $C_6$-$C_{12}$ aryl, $C_5$-$C_{12}$ heteroaryl, $C_1$-$C_{10}$ perfluoroalkyl, silicon-containing groups selected from the group consisting of silyl, alkylsilyl, perfluoroalkylsilyl, triarylsilyl and alkylsilylsilyl, $R^aR^bR^cNNR^c$, wherein $R^a$, $R^b$ and $R^c$ may be the same as or different from one another and each is independently selected from hydrogen and $C_1$-$C_6$ alkyl, and pendant ligands including functional group(s) providing further coordination to the metal center, including for example, aminoalkyl, alkoxyalkyl, aryloxyalkyl, imidoalkyl, and acetylalkyl Preferred substituent groups among the foregoing include H, $C_1$-$C_6$ alkyl, $C_1$-$C_6$ alkoxy, $C_6$-$C_{10}$ aryl, $C_3$-$C_6$ alkylsilyl, and pendant ligands including functional group(s) providing further coordination to the metal center, including for example, aminoalkyl, alkoxyalkyl, aryloxyalkyl, imidoalkyl, and acetylalkyl.

In addition to enhancing compound stability, the Lewis-base ligands will also lower the $t_{50}$ of the Ba and Sr compounds with respect to the corresponding compound uncomplexed with the Lewis-base. The lowering of the $t_{50}$ value is a result of the Lewis-base ligand disrupting intermolecular interactions.

Figure 2:
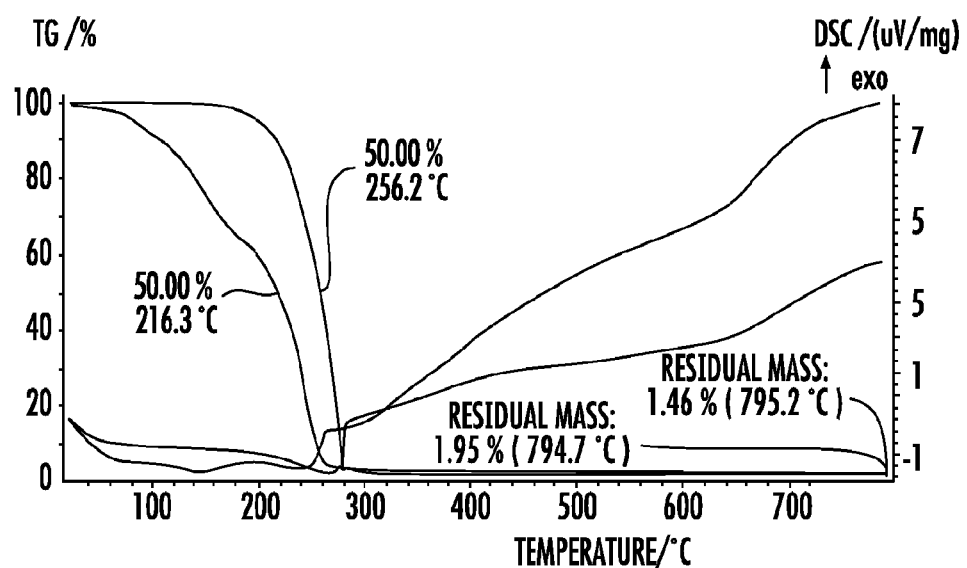
FIG. 2 is a plot of STA results for $Sr(Cp')_2$ and $Sr(Cp')_2$ (PMDETA).

The lowering of $t_{50}$ is evident from analysis of STA results for $Sr(Cp')_2$ and $Sr(Cp')_2(PMDETA)$, wherein Cp' is tetramethyl-n-propylcyclopentadienyl, and PMDETA is pentamethyl diethylene triamine. The simultaneous thermal analysis (STA) plot of thermogravimetric analysis (TGA) and differential scanning calorimetry (DSC) curves for such precursors is shown in FIG. 2 hereof, wherein the upper TGA curve represents $Sr(Cp')_2$ and the upper DSC curve represents $Sr(Cp')_2(PMDETA)$.

The $t_{50}$ value for $Sr(Cp')_2$ is 256° C. and the $t_{50}$ value for $Sr(Cp')_2(PMDETA)$ is 40° C. lower at 216° C. The Lewis-base adducts with lower $t_{50}$ values will enable lower transport temperatures to be employed in CVD, ALD and RVD processes.

The precursors of the invention can be readily synthesized with the skill of the art, with indenyl precursors being synthesized by a process of a general type as described in J. S. Overby and T. P. Hanusa, *Organometallics* 1996, 15, 2205, and cyclopentadienyl precursors being synthesized in an analogous manner with respect to corresponding cyclopentadienyl structure in place of the indene structure.

The precursors of the invention can be supplied in any suitable form for volatilization to produce the precursor vapor for deposition contacting with the substrate, e.g., in a liquid form that is vaporized or as a solid that is dissolved or suspended in a solvent medium for flash vaporization, as a sublimable solid, or as a solid having sufficient vapor pressure to render it suitable for vapor delivery to the deposition chamber, or in any other suitable form.

When solvents are employed for delivery of the precursors of the invention, any suitable solvent medium can be employed in which the precursor can be dissolved or dispersed for delivery. By way of example, the solvent medium may be a single-component solvent or a multicomponent solvent mixture, including solvent species such as $C_3$-$C_{12}$ alkanes, $C_2$-$C_{12}$ ethers, $C_6$-$C_{12}$ aromatics, $C_7$-$C_{16}$ arylalkanes, $C_{10}$-$C_{25}$ arylcyloalkanes, and further alkyl-substituted forms of aromatic, arylalkane and arylcyloalkane species, wherein the further alkyl substituents in the case of multiple alkyl substituents may be the same as or different from one another and wherein each is independently selected from $C_1$-$C_8$ alkyl. Illustrative solvents include amines, ethers, aromatic solvents, glymes, tetraglymes, alkanes, alkyl-substituted benzene compounds, benzocyclohexane (tetralin), alkyl-substituted benzocyclohexane and ethers, with tetrahydrofuran, xylene, 1,4-tertbutyltoluene, 1,3-diisopropylbenzene, dimethyltetralin, octane and decane being potentially useful solvent species in specific applications. In one embodiment, the solvent is selected from among tertiary amines, ethers and aromatic solvent.

In various embodiments of the invention, it may be desirable to utilize aromatic solvents such as xylene, 1,4-tertbutyltoluene, 1,3-diisopropylbenzene, tetralin, dimethyltetralin and other alkyl-substituted aromatic solvents. The solvent medium may also comprise a stabilizing solvent, e.g., a Lewis-base ligand.

In other applications, preferred solvents may include amine solvents, neutral amines such as DMAPA, octane or other aliphatic solvents, aromatic solvents such as toluene, ethers such as tetrahydrofuran (THF), and tetraglymes.

Thus, the precursors may be supplied in liquid delivery systems as individual precursors or mixtures of precursors, in solvent media that may be comprised of a single component solvent, or alternatively may be constituted by a solvent mixture, as appropriate in a given application. The solvents that may be employed for such purpose can be of any suitable type in which the specific precursor(s) can be dissolved or suspended, and subsequently volatilized to form the precursor vapor for contacting with the substrate on which the metal is to be deposited.

The invention also contemplates delivery of the precursor by bubbler delivery techniques, in which the bubbler is arranged to operate at or above the melting point of the precursor.

In general, the precursor compositions of the invention may alternatively comprise, consist, or consist essentially of any of the components and functional moieties disclosed herein, in specific embodiments of the invention.

Precursors of the invention can be utilized in combinations, in which two or more of such precursors are mixed with one another, e.g., in a solution as a precursor cocktail composition for liquid delivery.

Alternatively, the precursor species may be individually dissolved in solvent(s) and delivered into vaporizers for volatilization of the precursor solution to form a precursor vapor that then is transported to the deposition chamber of the deposition system to deposit the metal-containing film on a wafer or other microelectronic device substrate.

As a still further alternative, the precursors can be delivered by solid delivery techniques, in which the solid is volatilized to form the precursor vapor that then is transported to the deposition chamber, and with the solid precursor in the first instance being supplied in a packaged form for use, e.g., in a ProE-Vap package (ATMI, Inc., Danbury, Conn., USA).

The precursors of the present invention are usefully employed for forming metal-containing thin films of high conformality and uniformity characteristics, by ALD, RVD and CVD processes. The process conditions for the deposition process in a specific application may be readily determined empirically by variation of specific conditions (temperature, pressure, flow rate, concentration, etc.) and characterization of the resulting film deposit.

The precursors can be volatilized for the deposition of metal-containing films in any suitable manner and using any suitable vaporizer apparatus or technique. The precursors may be vaporized singly and separately, or they may be volatilized in admixture or solution with one another.

In the formation of metal-containing films, any suitable co-reactant or carrier species may be employed, e.g., oxidants, producing agents, inert gases, etc. In a specific embodiment in which an oxidant is used, the oxidant employed in the deposition may be of any suitable type, e.g., nitrous oxide, oxygen, ozone, water, alcohols, combinations of two or more compatible oxidant species selected from such oxidants, or other suitable oxidant. The co-reactants may be supplied simultaneously, e.g., with the precursors entering the deposition chamber concurrently, in a chemical vapor deposition mode, or separately from the precursors, in an atomic layer deposition or digital CVD mode. The precursors can be employed in an ALD mode, in which a purge pulse separates them from the co-reactants, and matched or unmatched precursors may be used.

By way of specific example, an atomic layer deposition process for forming a layer of strontium titanate on a substrate can be carried out involving pulsing of a titanium source into a deposition reactor, purging the reactor to remove excess titanium precursor, then pulsing water vapor into the reactor, with or without oxidant (such as $O_2$, $O_3$ or $N_2O$,) followed by pulsing a strontium source into the reactor and then purging, followed by introduction of water vapor with or without oxidant. This process is repeated until a desired film thickness of the strontium titanate layer is reached. Deposition temperature can for example be in a range of from 250° C. to 500° C. Pulse rates can be on the order from 10 milliseconds to 30 seconds or more. After deposition, the film may require rapid thermal annealing (RTA) to obtain a crystalline $SrTiO_3$ film, e.g., by RTA treatment at temperature in a range of from 500° C. to 900° C., for an annealing period of from a few seconds to 30 minutes or more.

In one embodiment of the above-described process, the oxidant is selected from among oxygen, ozone and oxygen plasma. The use of such oxidant may eliminate the need for a final annealing step, such as rapid thermal annealing. It is noted that formation of the metal-containing film will require oxidant, but in atomic layer deposition processes, when the metal precursor vapor is in contact with the substrate, the presence of an oxidant is not required.

The metal films of the invention may be subjected to any suitable post-deposition processing steps, e.g., annealing, oxidizing, reducing, etc., as appropriate to the specific metal film involved.

Metal films formed in accordance with the invention may be of any suitable type and include, without limitation, films of metal oxides, metal nitrides, metal hafnates, metal titanates, metal lanthannates, metal ruthenates, metal oxynitrides, metal silicates, and metal silicides, wherein the metal includes barium and/or strontium.

In general, the thicknesses of the metal-containing layers in the practice of the present invention can be of any suitable value. In a specific embodiment of the invention, the thickness of the metal-containing layer can be in a range of from 2 nm to 500 nm or more.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_8$ alkyl, or any other sub-range within the broad carbon number range.

The precursors of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^1$ is $C_1$-$C_{12}$ alkyl, with the proviso that $R^i \neq C_4$ alkyl when $R^j$ is silyl.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention.

Figure 3:
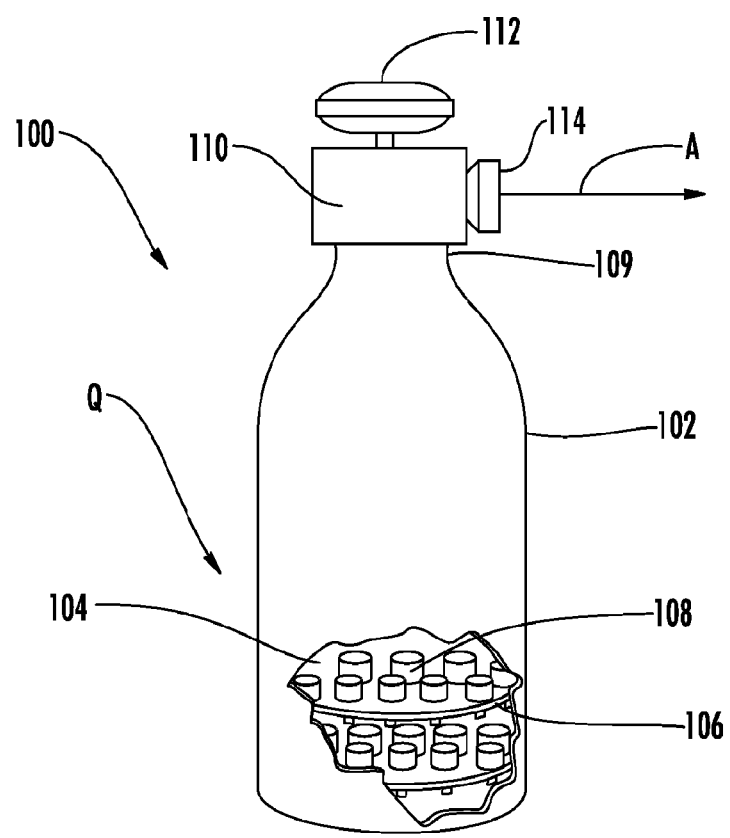
FIG. 3 is a schematic representation of a material storage and dispensing package containing a precursor of the present invention, in one embodiment thereof.

FIG. 3 is a schematic representation of a material storage and dispensing package 100 containing a barium or strontium precursor, according to one embodiment of the present invention.

The material storage and dispensing package 100 includes a vessel 102 that may for example be of generally cylindrical shape as illustrated, defining an interior volume 104 therein. In this specific embodiment, the precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 1).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

INDUSTRIAL APPLICABILITY

The precursors of the invention are usefully employed to form precursor vapor for contacting with a substrate to deposit a barium- and/or strontium-containing thin film thereon. Precursors of the invention can be employed to conduct atomic layer deposition, yielding ALD films of superior conformality that are uniformly coated on the substrate with high step coverage and conformality even on high aspect ratio structures. The precursors of the invention enable a wide variety of microelectronic devices, e.g., semiconductor products, flat panel displays, etc., to be fabricated with barium- and/or strontium-containing films of superior quality.

What is claimed is:

1. A method of depositing a strontium titanate film on a substrate, comprising carrying out an atomic layer deposition (ALD) process with strontium and titanium precursors, wherein the strontium precursor is bis(n-propyltetramethylcyclopentadienyl)strontium.

2. The method of claim 1, wherein the precursor is dissolved in a solvent medium.

3. The method of claim 2, wherein the solvent in the solvent medium is a single-component solvent or a multicomponent solvent mixture.

4. The method of claim 3, wherein the solvent medium is selected from the group consisting of $C_3$-$C_{12}$ alkanes, $C_2$-$C_{12}$ ethers, $C_6$-$C_{12}$ aromatics, $C_7$-$C_{16}$ arylalkanes, $C_{10}$-$C_{25}$ arylcyloalkanes, and further alkyl-substituted forms of the aromatic, arylalkane and arylcyloalkane species, wherein the further alkyl substituents in the case of multiple alkyl substituents may be the same as or different from one another and wherein each is independently selected from $C_1$-$C_8$ alkyl.

5. The method of claim 1, wherein the precursor is in liquid form and is vaporized for vapor delivery in the atomic layer deposition process.

* * * * *

UNITED STATES PATENT AND TRADEMARK OFFICE
CERTIFICATE OF CORRECTION

PATENT NO. : 8,455,049 B2
APPLICATION NO. : 12/672684
DATED : June 4, 2013
INVENTOR(S) : Thomas M. Cameron et al.

It is certified that error appears in the above-identified patent and that said Letters Patent is hereby corrected as shown below:

In the Specification

Column 5, line 27: "...$C_5$-$C_{12}$ heteroaryl, perfluoroalkyl..." should be -- ...$C_5$-$C_{12}$ heteroaryl, $C_1$-$C_{10}$ perfluoroalkyl... --.

Column 5, line 49: "...and acetylalkyl Ligands may..." should be
-- ... and acetylalkyl. Ligands may... --.

Column 8, line 65: "...and acetylalkyl Preferred..." should be -- ... and acetylalkyl. Preferred... --.

Column 12, line 12: "...$C_3$-$C_8$ alkyl..." should be -- ...$C_3$-$C_5$ alkyl... --.

Column 12, line 19: "...wherein $R^1$ is..." should be -- ... wherein $R^i$ is ... --.

In the Claims

Column 14, lines 44-45: "...further alkyl [hard return] substituents..." should be
-- ...further alkyl substituents... --.

Signed and Sealed this
Twenty-seventh Day of August, 2013

Teresa Stanek Rea
*Acting Director of the United States Patent and Trademark Office*